US006241784B1

(12) United States Patent
De La Mettrie et al.

(10) Patent No.: US 6,241,784 B1
(45) Date of Patent: Jun. 5, 2001

(54) OXIDIZING COMPOSITION AND USES FOR DYEING, FOR PERMANENTLY SETTING OR BLEACHING KERATIN FIBRES

(75) Inventors: Roland De La Mettrie, Le Vesinet; Jean Cotteret, Verneuil sur Seine; Arnaud De Labbey, Aulnay Sous Bois; Mireille Maubru, Chatou, all of (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/319,163

(22) PCT Filed: Sep. 22, 1998

(86) PCT No.: PCT/FR98/02024

§ 371 Date: Jun. 2, 1999

§ 102(e) Date: Jun. 2, 1999

(87) PCT Pub. No.: WO99/17721

PCT Pub. Date: Apr. 15, 1999

(30) Foreign Application Priority Data

Oct. 3, 1997 (FR) .................................... 97/12356

(51) Int. Cl.$^7$ ..................................................... A61K 7/13
(52) U.S. Cl. ................... 8/406; 8/401; 8/563; 424/70.14
(58) Field of Search ............................... 8/401, 561, 406, 8/408, 409, 410, 411, 412; 427/70.11, 70.13

(56) References Cited

U.S. PATENT DOCUMENTS

| 3,893,803 | 7/1975 | Kaiser ..................................... 424/94 |
| 3,907,799 | 9/1975 | O'Brien et al. ..................... 260/256.4 |
| 4,961,925 | * 10/1990 | Tsujino et al. ......................... 424/71 |
| 5,679,328 | * 10/1997 | Dupuis .............................. 424/70.13 |
| 5,685,882 | * 11/1997 | Samain et al. ........................... 8/408 |
| 6,027,719 | * 2/2000 | Tomura et al. ................... 424/78.02 |
| 6,080,391 | * 6/2000 | Tsuchiya et al. ....................... 424/65 |

FOREIGN PATENT DOCUMENTS

| 2 359 399 | 6/1975 | (DE) . |
| 3 843 892 | 6/1990 | (DE) . |
| 4 133 957 | 4/1993 | (DE) . |
| 195 43 988 | 5/1997 | (DE) . |
| 195 47 991 | 6/1997 | (DE) . |
| 0 310 675 | 4/1989 | (EP) . |
| 0 550 106 | 7/1993 | (EP) . |
| 0 550 656 | 7/1993 | (EP) . |
| 0 628 559 | 12/1994 | (EP) . |
| 0 716 846 | 6/1996 | (EP) . |
| 0 795 313 | 9/1997 | (EP) . |
| 2 112 550 | 6/1972 | (FR) . |
| 2 586 913 | 3/1987 | (FR) . |
| 2 733 749 | 11/1996 | (FR) . |
| 1 153 196 | 5/1969 | (GB) . |
| 1 026 978 | 4/1996 | (GB) . |
| 63-169571 | 7/1988 | (JP) . |
| WO 94/00100 | 1/1994 | (WO) . |
| WO 94/08969 | 4/1994 | (WO) . |
| WO 94/08970 | 4/1994 | (WO) . |
| WO 94/12511 | 6/1994 | (WO) . |
| WO 96/15765 | 5/1996 | (WO) . |

OTHER PUBLICATIONS

English language Derwent Abstract of 2 733 749.
English language Derwent Abstract of JP 63–169571.
Ermitas Alcade et al., "Etude de la réaction du β–aminocrotonitrile et du αformyl phénylacétonitrile avec l'hydrazine: synthése d'amino–7 pyrazolo[1,5–α]pyrimidines", Journal of Heterocyclic Chemistry, vol. 11, No. 3, Jun. 1974, pp. 423–429.
Nadia S. Ibrahim et al., "Studies on 3,5–Diaminopyrazoles: Synthesis of New Polyfunctionally Substituted Pyrazoloazines and Pyrazoloazoles", Archiv der Pharmazie vol. 320, No. 3, Mar. 1987, pp. 240–246.
Alexander McKillop et al., "Reaction of Hydrazine With β–Aminocrotononitrile: Synthesis of 2,7–dimethyl–5–aminopyrazolo[1,5–α]pyrimidine", Heterocycles, vol. 6, No. 9, 10, 1977, pp. 1355–1360.
Thomas Novinson et al., "Synthesis and Antifungal Properties of Certain 7–alkylaminopyrazolo[1,5–α]pyrimidines", Journal of Medicinal Chemistry, vol. 20, No. 2, 1977, pp. 296–299.
Vishnu J. Ram et al., "Synthesis of bioisosteric pyrazolo[1,5–α]pyrimidines as leishmanicides", Indian Journal of Chemistry, vol. 34B, Jun. 1995, pp. 514–520.
Koji Saito et al., "The Reaction of Ethyl Ethyoxymethylenecyanoacetate with Its Hydrazino Derivatives", Bulletin of the Chemical Society of Jpan, vol. 47, No. 2, 1974, pp. 476–480.
Robert H. Springer et al., "Synthesis and Enzymic–Activity of 6–Carbethoxy–and 6–Ethoxy–3, 7–disubstituted–pyrazolo[1,5–α]pyrimidines and Related Derivatives as Adenosine Cyclic 3', 5'–Phosphate Phosphodiesterase Inhibitors", Journal of Medicinal Chemistry, vol. 25, No. 3, 1982, pp. 235–242.

* cited by examiner

Primary Examiner—Yogendra Gupta
Assistant Examiner—Derrick G. Hamlin
(74) Attorney, Agent, or Firm—Finnegan, Henderson, Farabow, Garrett & Dunner, L.L.P.

(57) ABSTRACT

The present application relates to a cosmetic composition intended for treating keratin fibers, comprising, in a support which is suitable for keratin fibres:

(a) at least one enzyme of 2-electron oxidoreductase type in the presence of at least one donor for the said enzyme;

(b) at least one nonionic guar gum;

as well as to processes for treating keratin fibers, in particular processes for dyeing, permanently reshaping or bleaching the hair, using this composition.

28 Claims, No Drawings

OXIDIZING COMPOSITION AND USES FOR DYEING, FOR PERMANENTLY SETTING OR BLEACHING KERATIN FIBRES

The present invention relates to an oxidizing composition intended for treating keratin fibres, comprising at least one enzyme of 2-electron oxidoreductase type in the presence of at least one donor for the said enzyme and at least one nonionic guar gum, as well as to its uses for dyeing, for permanently reshaping or for bleaching keratin fibres, in particular human hair.

It is known to dye keratin fibres, and in particular human hair, with dye compositions containing oxidation dye precursors, in particular para-phenylenediamines, ortho- or para-aminophenols and heterocyclic bases which are generally referred to as oxidation bases. Oxidation dye precursors, or oxidation bases, are colourless or weakly coloured compounds which, when combined with oxidizing products, can give rise to coloured compounds and dyes by a process of oxidative condensation.

It is also known that the shades obtained with these oxidation bases can be varied by combining them with couplers or colour modifiers, the latter being chosen in particular from aromatic meta-diamines, meta-aminophenols, meta-diphenols and certain heterocyclic compounds.

The variety of compounds used as regards the oxidation bases and the couplers allows a wide range of colours to be obtained.

The so-called "permanent" coloration obtained by means of these oxidation dyes must moreover satisfy a certain number of requirements. Thus it must have no toxicological drawbacks, it must be able to give shades of the desired intensity and it must be able to withstand external agents (light, bad weather, washing, permanent-waving, perspiration, rubbing).

The dyes must also be able to cover white hair and, lastly, they must be as unselective as possible, i.e. they must give the smallest possible colour differences along the same length of keratin fibre, which may in fact be differently sensitized (i.e. damaged) between its tip and its root.

The oxidation dyeing of keratin fibres is generally carried out in alkaline medium, in the presence of hydrogen peroxide. However, the use of alkaline media in the presence of hydrogen peroxide has the drawback of causing appreciable degradation of the fibres, as well as considerable bleaching of the keratin fibres, which is not always desirable.

The oxidation dyeing of keratin fibres can also be carried out using oxidizing systems other than hydrogen peroxide, such as enzymatic systems. Thus, it has already been proposed to dye keratin fibres, in particular in patent application EP-A-0,310,675, with compositions comprising an oxidation dye precursor in combination with enzymes such as pyranose oxidase, glucose oxidase or uricase, in the presence of a donor for the said enzymes. Although being used under conditions which do not result in degradation of the keratin fibres which is comparable to that caused by the dyes used in the presence of hydrogen peroxide, these dye formulations nevertheless lead to colorations which are still insufficient, both as regards the homogeneity of the colour distributed along the fibre ("unison") and as regards the chromaticity (luminosity), the dyeing power and the resistance to the various aggressive factors to which the hair may be subjected.

It is known that the most common technique for obtaining a permanent reshaping of the hair consists, in a first stage, in opening the keratin —S—S-disulphide (cysteine) bonds using a composition containing a suitable reducing agent (reduction step) followed, after having rinsed the head of hair thus treated, by reconstituting, in a second stage, the said disulphide bonds by applying to the hair, which has been placed under tension beforehand (rollers and the like), an oxidizing composition (oxidation step, also known as the fixing step) so as finally to give to the hair the desired shape. This technique thus makes it equally possible either to make the hair wavy or to straighten it or to remove its curliness. The new shape given to the hair by a chemical treatment such as above is remarkably long-lasting and in particular resists the action of washing with water or shampoos, as opposed to simple standard techniques for temporary reshaping, such as hairsetting.

The reducing compositions which may be used in order to carry out the first step of a permanent-waving operation generally contain, as reducing agents, sulphites, bisulphites, alkylphosphines or, preferably, thiols. Among the thiols, those commonly used are cysteine and the various derivatives thereof, cysteamine and the derivatives thereof, thiolactic acid or thioglycolic acid, the salts thereof and the esters thereof, in particular glyceryl thioglycolate.

As regards the oxidizing compositions needed to carry out the fixing step, use is usually made in practice of compositions based on aqueous hydrogen peroxide, sodium bromate or persalts such as sodium perborate, which have the drawback of being liable to damage the hair.

The problem of the technique of the permanent-waving operations known to date is that their application to the hair induces long-term adverse changes in the quality of the hair. The essential causes of these adverse changes in the quality of the hair are a reduction in its cosmetic properties, such as its sheen and its feel, and degradation of its mechanical properties, more particularly degradation of its mechanical strength due to swelling of the keratin fibres during the rinsing between the reduction step and the oxidation step, which can also be reflected by an increase in its porosity. The hair is weakened and can become brittle during subsequent treatments such as blow-drying.

The same problem of adverse changes in keratin fibres is encountered during processes for bleaching the hair.

It is known that the permanent reshaping or bleaching of keratin fibres can also be carried out under milder conditions using oxidizing systems other than hydrogen peroxide, such as enzymatic systems. Thus, processes for the permanent reshaping or bleaching of keratin fibres have already been proposed, in particular in patent application EP-A-0,310,675, with compositions comprising an enzyme such as pyranose oxidase, glucose oxidase or uricase, in the presence of a donor for the said enzyme. Although being used under conditions which do not result in degradation of the keratin fibres which is comparable to that caused by conventional permanent-waving or bleaching processes, these oxidizing formulations nevertheless lead to results which are still insufficient, as regards the curl hold over time, as regards the compatibility of permanent-waved or bleached hair with subsequent treatments, as regards the reduction of the mechanical properties of the permanent-waved hair, in particular the reduction of the porosity of the hair, and as regards the reduction of the cosmetic properties such as the feel, or alternatively as regards the uniformity of the bleaching along the keratin fibres.

The aim of the present invention is to solve the problems mentioned above.

The Applicant has discovered, surprisingly, novel compositions containing, as oxidizing system, at least one enzyme of 2-electron oxidoreductase type in the presence of at least one donor for the said enzyme and at least one nonionic guar gum, which can constitute, in the presence of oxidation dye precursors (oxidation bases) and optionally couplers, ready-to-use dye formulations which lead to more homogeneous, more intense and more chromatic colorations without giving rise to any significant degradation, these colorations being relatively unselective and showing good resistance to the various aggressive factors to which the hair may be subjected.

The Applicant has also discovered, unexpectedly, that the use, in a process for the permanent reshaping of keratin fibres, of an oxidizing composition containing, as oxidizing system, at least one enzyme of 2-electron oxidoreductase typein the presence of at least one donor for the said enzyme and at least one nonionic guar gum, makes it possible to solve the technical problems mentioned above. In particular, this type of oxidizing composition improves the curl hold obtained over time, substantially reduces the porosity of permanent-waved hair and improves the compatibility of permanent-waved hair with respect to subsequent treatments.

The Applicant has also discovered, surprisingly, that the use, in a process for bleaching keratin fibres, of an oxidizing composition containing, as oxidizing system, at least one enzyme of 2-electron oxidoreductase typein the presence of at least one donor for the said enzyme and at least one nonionic guar gum makes it possible to solve the technical problems mentioned above, in particular to improve the compatibility of bleached hair with respect to subsequent treatments. This type of oxidizing composition gives a more uniform bleaching effect on the hair and improves the cosmetic properties, such as the feel.

These discoveries form the basis of the present invention.

The subject of the present invention is thus, firstly, a cosmetic and/or dermatological composition intended for treating keratin fibres, in particular human keratin fibres and more particularly human hair, comprising, in a support which is suitable for keratin fibres:

(a) at least one enzyme of 2-electron oxidoreductase type in the presence of at least one donor for the said enzyme, (b) at least one nonionic guar gum.

The 2-electron oxidoreductase(s) used in the oxidizing compositions in accordance with the invention can be chosen in particular from pyranose oxidases, glucose oxidases, glycerol oxidases, lactate oxidases, pyruvate oxidases and uricases.

According to the invention, the 2-electron oxidoreductase is preferably chosen from uricases of animal, microbiological or biotechnological origin.

By way of example, mention may be made of uricase extracted from boar liver, urlcase from *Arthrobacter globiformis*, as well as uricase from *Aspergillus flavus*.

The 2-electron oxidoreductase(s) can be used in pure crystalline form or in a form diluted in a diluent which is inert with respect to the said 2-electron oxidoreductase.

The 2-electron oxidoreductase(s) in accordance with the invention preferably represent(s) from 0.01 to 20% by weight approximately relative to the total weight of the composition, and even more preferably from 0.1 to 5% by weight approximately relative to this weight.

According to the invention, the term donor is understood to refer to the various substrates also necessary for the functioning of the said 2-electron oxidoreductase(s).

The nature of the donor (or substrate) for the said enzyme varies depending on the nature of the 2-electron oxidoreductase used. For example, as donors for the pyranose oxidases, mention may be made of D-glucose, L-sorbose and D-xylose; as a donor for the glucose oxidases, mention may be made of D-glucose; as donors for the glycerol oxidases, mention may be made of glycerol and dihydroxyacetone; as donors for the lactate oxidases, mention may be made of lactic acid and its salts; as donors for the pyruvate oxidases, mention may be made of pyruvic acid and its salts; and lastly, as donors for the uricases, mention may be made of uric acid and its salts.

The donor(s) (or substrate(s)) used in accordance with the invention preferably represent from 0.01 to 20% by weight approximately relative to the total weight of the composition in accordance with the invention, and even more preferably from 0.1 to 5% approximately relative to this weight.

According to the invention, unmodified or chemically modified nonionic guar gums can be used.

The unmodified nonionic guar gums are, for example, the products sold under the name Vidogum GH 175 by the company Unipectine and under the name Jaguar C by the company Meyhall.

The nonionic guar gums which can be used according to the invention are preferably modified with $C_1$–$C_6$ hydroxyalkyl groups.

Among the hydroxyalkyl groups, mention may be made, for example, of hydroxymethyl, hydroxyethyl, hydroxypropyl and hydroxybutyl groups.

These guar gums are well known in the state of the art and can be prepared, for example, by reacting corresponding alkene oxides, such as, for example, propylene oxides, with the guar gum, so as to obtain a guar gum modified with hydroxypropyl groups.

The degree of hydroxyalkylation, which corresponds to the number of alkylene oxide molecules consumed by the number of free hydroxyl functions present on the guar gum, preferably ranges from 0.4 to 1.2.

Such nonionic guar gums optionally modified with hydroxyalkyl groups are sold, for example, under the trade names Jaguar HP8, Jaguar HP60 and Jaguar HP120, Jaguar DC 293 and Jaguar HP 105 by the company Rhône-Poulenc (Meyhall) or under the name Galactasol 4H4FD2 by the company Aqualon.

The concentration of nonionic guar gum can range from 0.01 to 10% by weight approximately relative to the total weight of the composition, and preferably between 0.1 and 5% approximately.

A subject of the present invention is also a ready-to-use composition for the oxidation dyeing of keratin fibres, and in particular human keratin fibres such as the hair, of the type comprising, in a medium which is suitable for dyeing, at least one oxidation base and, where appropriate, one or more couplers, which is characterized in that it contains:

(a) at least one enzyme of 2-electron oxidoreductase type in the presence of at least one donor for the said enzyme, (b) at least one nonionic guar gum.

The nature of the oxidation base(s) used in the ready-to-use dye composition is not a critical factor. They can be chosen, in particular, from para-phenylenediamines, double bases, para-aminophenols, ortho-aminophenols and heterocyclic oxidation bases.

Among the para-phenylenediamines which can be used as oxidation bases in the dye compositions in accordance with the invention, mention may be made in particular of the compounds of formula (I) below, and the addition salts thereof with an acid:

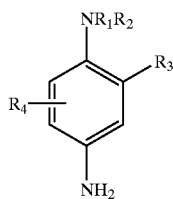

(I)

in which:
- $R_1$ represents a hydrogen atom, a $C_1$–$C_4$ alkyl radical, a $C_1$–$C_4$ monohydroxyalkyl radical, a $C_2$–$C_4$ polyhydroxyalkyl radical, a $(C_1$–$C_4)$alkoxy$(C_1$–$C_4)$alkyl radical, a $C_1$–$C_4$ alkyl radical substituted with a nitrogenous group, a phenyl radical or a 4'-aminophenyl radical;
- $R_2$ represents a hydrogen atom, a $C_1$–$C_4$ alkyl radical, a $C_1$–$C_4$ monohydroxyalkyl radical, a $C_2$–$C_4$ polyhydroxyalkyl radical, a $(C_1$–$C_4)$alkoxy$(C_1$–$C_4)$alkyl radical or a $C_1$–$C_4$ alkyl radical substituted with a nitrogenous group;
- $R_3$ represents a hydrogen atom, a halogen atom such as a chlorine, bromine, iodine or fluorine atom, a $C_1$–$C_4$ alkyl radical, a $C_1$–$C_4$ monohydroxyalkyl radical, a $C_1$–$C_4$ hydroxyalkoxy radical, an acetylamino$(C_1$–$C_4)$ alkoxy radical, a $C_1$–$C_4$ mesylaminoalkoxy radical or a carbamoylamino$(C_1$–$C_4)$alkoxy radical,
- $R_4$ represents a hydrogen or halogen atom or a $C_1$–$C_4$ alkyl radical.

Among the nitrogenous groups of formula (I) above, mention may be made in particular of amino, mono$(C_1$–$C_4)$alkylamino, di$(C_1$–$C_4)$alkylamino, tri$(C_1$–$C_4)$-alkylamino, monohydroxy$(C_1$–$C_4)$alkylamino, imidazolinium and ammonium radicals.

Among the para-phenylenediamines of formula (I) above, mention may be made more particularly of para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-2-methylaniline, 4-amino-2-chloro-N,N-bis(β-hydroxyethyl)aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(βγ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine and N-(β-methoxyethyl)-para-phenylenediamine, and the addition salts thereof with an acid.

Among the para-phenylenediamines of formula (I) above, para-phenylenediamine, para-toluylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine and the addition salts thereof with an acid are most particularly preferred.

According to the invention, the term double bases is understood to refer to the compounds containing at least two aromatic rings bearing amino and/or hydroxyl groups.

Among the double bases which can be used as oxidation bases in the dye compositions in accordance with the invention, mention may be made in particular of the compounds corresponding to formula (II) below, and the addition salts thereof with an acid:

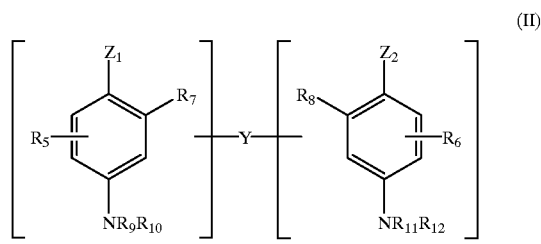

(II)

in which:
- $Z_1$ and $Z_2$, which may be identical or different, represent a hydroxyl or —$NH_2$ radical which may be substituted with a $C_1$–$C_4$ alkyl radical or with a linker arm Y;
- the linker arm Y represents a linear or branched alkylene chain containing from 1 to 14 carbon atoms, which may be interrupted by or terminated with one or more nitrogenous groups and/or one or more hetero atoms such as oxygen, sulphur or nitrogen atoms, and optionally substituted with one or more hydroxyl or $C_1$–$C_4$ alkoxy radicals;
- $R_5$ and $R_6$ represent a hydrogen or halogen atom, a $C_1$–$C_4$ alkyl radical, a $C_1$–$C_4$ monohydroxyalkyl radical, a $C_2$–$C_4$ polyhydroxyalkyl radical, a $C_1$–$C_4$ aminoalkyl radical or a linker arm Y;
- $R_7$, $R_8$, $R_9$, $R_{10}$, $R_{11}$ and $R_{12}$, which may be identical or different, represent a hydrogen atom, a linker arm Y or a $C_1$–$C_4$ alkyl radical; it being understood that the compounds of formula (II) contain only one linker arm Y per molecule.

Among the nitrogenous groups of formula (II) above, mention may be made in particular of amino, mono$(C_1$–$C_4)$alkylamino, di$(C_1$–$C_4)$alkylamino, tri$(C_1$–$C_4)$alkylamino, monohydroxy$(C_1$–$C_4)$alkylamino, imidazolinium and ammonium radicals.

Among the double bases of formula (II) above, mention may be made more particularly of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl) tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis-(ethyl)-N,N'-bis(4'-amino-3'-methylphenyl)ethylenediamine and 1,8-bis(2,5-diaminophenoxy)-3,5-dioxaoctane, and the addition salts thereof with an acid.

Among these double bases of formula (II), N,N'-bis(β-hydroxyethyl)-N,N'-bis(4'-aminophenyl)-1,3-diaminopropanol and 1,8-bis(2,5-diaminophenoxy)-3,5-dioxaoctane, or one of the addition salts thereof with an acid, are particularly preferred.

Among the para-aminophenols which can be used as oxidation bases in the dye compositions in accordance with the invention, mention may be made in particular of the compounds corresponding to formula (III) below, and the addition salts thereof with an acid:

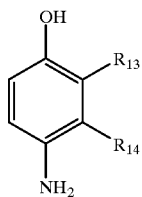

(III)

in which:
  $R_{13}$ represents a hydrogen or halogen atom or a $C_1$–$C_4$ alkyl, $C_1$–$C_4$ monohydroxyalkyl, $(C_1$–$C_4)$alkoxy $(C_1$–$C_4)$alkyl, $C_1$–$C_4$ aminoalkyl or hydroxy$(C_1$–$C_4)$ alkylamino$(C_{1-C4})$alkyl radical,
  $R_{14}$ represents a hydrogen or halogen atom or a $C_1$–$C_4$ alkyl, $C_1$–$C_4$ monohydroxyalkyl, $C_2$–$C_4$ polyhydroxyalkyl, $C_1$–$C_4$ aminoalkyl, $C_1$–$C_4$ cyanoalkyl or $(C_1$–$C_4)$alkoxy-$(C_1$–$C_4)$alkyl radical, it being understood that at least one of the radicals $R_{13}$ or $R_{14}$ represents a hydrogen atom.

Among the para-aminophenols of formula (III) above, mention may be made more particularly of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols which can be used as oxidation bases in the dye compositions in accordance with the invention, mention may be made more particularly of 2-aminophenol, 2-amino-5-methylphenol, 2-amino-6-methylphenol and 5-acetamido-2-aminophenol, and the addition salts thereof with an acid.

Among the heterocyclic bases which can be used as oxidation bases in the dye compositions in accordance with the invention, mention may be made more particularly of pyridine derivatives, pyrimidine derivatives, pyrazole derivatives and pyrazolopyrimidine derivatives, and the addition salts thereof with an acid.

Among the pyridine derivatives, mention may be made more particularly of the compounds described, for example, in patents GB 1,026,978 and GB 1,153,196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the addition salts thereof with an acid.

Among the pyrimidine derivatives, mention may be made more particularly of the compounds described, for example, in German patent DE 2,359,399 or Japanese patent JP 88-169,571 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and the addition salts thereof with an acid.

Among the pyrazole derivatives, mention may be made more particularly of the compounds described in patents DE 3,843,892, DE 4,133,957 and patent applications WO 94/08969, WO 94/08970, FR-A-2,733,749 and DE 195 43 988, such as 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof with an acid.

Among the pyrazolopyrimidine derivatives, mention may be made more particularly of the pyrazolo[1,5-a]pyrimidines of formula (IV) below, and the addition salts thereof with an acid or with a base and the tautomeric forms thereof, when a tautomeric equilibrium exists:

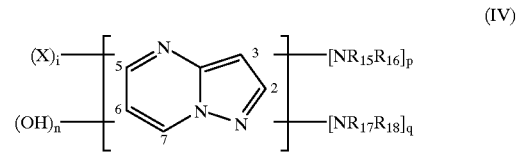

(IV)

in which:
  $R_{15}$, $R_{16}$, $R_{17}$ and $R_{18}$, which may be identical or different, denote a hydrogen atom, a $C_1$–$C_4$ alkyl radical, an aryl radial, a $C_1$–$C_4$ hydroxyalkyl radical, a $C_2$–$C_4$ polyhydroxyalkyl radical, a $(C_1$–$C_4)$alkoxy$(C_1$–$C_4)$alkyl radical, a $C_1$–$C_4$ aminoalkyl radical (it being possible for the amine to be protected with an acetyl, ureido or sulphonyl radical), a $(C_1$–$C_4)$alkylamino$(C_1$–$C_4)$alkyl radical, a di[$(C_1$–$C_4)$alkyl]amino$(C_1$–$C_4)$alkyl radical (it being possible for the dialkyl radicals to form a 5- or 6-membered carbon-based ring or a heterocycle), a hydroxy$(C_1$–$C_4)$alkyl- or di[hydroxy-$(C_1$–$C_4)$alkyl]amino$(C_1$–$C_4)$alkyl radical;
  the radicals X, which may be identical or different, denote a hydrogen atom, a $C_1$–$C_4$ alkyl radical, an aryl radical, a $C_1$–$C_4$ hydroxyalkyl radical, a $C_2$–$C_4$ polyhydroxyalkyl radical, a $C_1$–$C_4$ aminoalkyl radical, a $(C_1$–$C_4)$ alkylamino$(C_1$–$C_4)$alkyl radical, a di[$(C_1$–$C_4)$alkyl]amino$(C_1$–$C_4)$alkyl radical (it being possible for the dialkyls to form a 5- or 6-membered carbon-based ring or a heterocycle), a hydroxy$(C_1$–$C_4)$alkyl- or di-[hydroxy$(C_1$–$C_4)$alkyl]amino$(C_1$–$C_4)$alkyl radical, an amino radical, a $(C_1$–$C_4)$alkyl- or di[$(C_1$–$C_4)$alkyl] amino radical; a halogen atom, a carboxylic acid group or a sulphonic acid group;
  i is equal to 0, 1, 2 or 3;
  p is equal to 0 or 1;
  q is equal to 0 or 1;
  n is equal to 0 or 1;
with the proviso that:
  the sum p+q is other than 0;
  when p+q is equal to 2, then n is equal to 0 and the groups $NR_{15}R_{16}$ and $NR_{17}R_{18}$ occupy the (2,3); (5,6); (6,7); (3,5) or (3,7) positions;

when p+q is equal to 1, then n is equal to 1 and the group NR$_{15}$R$_{16}$ (or NR$_{17}$R$_{18}$) and the OH group occupy the (2,3); (5,6); (6,7); (3,5) or (3,7) positions.

When the pyrazolo[1,5-a]pyrimidines of formula (IV) above are such that they contain a hydroxyl group on one of the positions 2, 5 or 7 α to a nitrogen atom, a tautomeric equilibrium exists represented, for example, by the following scheme:

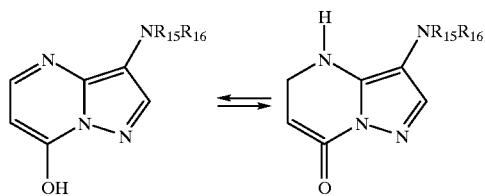

Among the pyrazolo[1,5-a]pyrimidines of formula (IV) above, mention may be made in particular of:
pyrazolo[1,5-a]pyrimidine-3,7-diamine;
2,5-dimethylpyrazolo[1,5-a]pyrimidine-3,7-diamine;
pyrazolo[1,5-a]pyrimidine-3,5-diamine;
2,7-dimethylpyrazolo[1,5-a]pyrimidine-3,5-diamine;
3-aminopyrazolo[1,5-a]pyrimidin-7-ol;
3-aminopyrazolo[1,5-a]pyrimidin-5-ol;
2-(3-aminopyrazolo[1,5-a]pyrimidin-7-ylamino)ethanol;
2-(7-aminopyrazolo[1,5-a]pyrimidin-3-ylamino)ethanol;
2-[(3-aminopyrazolo[1,5-a]pyrimidin-7-yl)-(2-hydroxyethyl)amino]ethanol;
2-[(7-aminopyrazolo[1,5-a]pyrimidin-3-yl)-(2-hydroxyethyl)amino]ethanol;
5,6-dimethylpyrazolo[1,5-a]pyrimidine-3,7-diamine;
2,6-dimethylpyrazolo[1,5-a]pyrimidine-3,7-diamine;
2,5,N7,N7-tetramethylpyrazolo[1,5-a]pyrimidine-3,7-diamine; and the addition salts thereof and the tautomeric forms thereof, when a tautomeric equilibrium exists.

The pyrazolo[1,5-a]pyrimidines of formula (IV) above can be prepared by cyclization starting with an aminopyrazole, according to the syntheses described in the following references:

EP 628559 Beiersdorf-Lilly.
R. Vishdu, H. Navedul, Indian J. Chem., 34b (6), 514, 1995.
N. S. Ibrahim, K. U. Sadek, F. A. Abdel-Al, Arch. Pharm., 320, 240, 1987.
R. H. Springer, M. B. Scholten, D. E. O'Brien, T. Novinson, J. P. Miller, R. K. Robins, J. Med. Chem., 25, 235, 1982.
T. Novinson, R. K. Robins, T. R. Matthews, J. Med. Chem., 20, 296, 1977.
U.S. Pat. No. 3,907,799 ICN Pharmaceuticals.

The pyrazolo[1,5-a]pyrimidines of formula (IV) above can also be prepared by cyclization starting from hydrazine, according to the syntheses described in the following references:

A. McKillop and R. J. Kobilecki, Heterocycles, 6(9), 1355, 1977.
E. Alcade, J. De Mendoza, J. M. Marcia-Marquina, C. Almera, J. Elguero, J. Heterocyclic Chem., 11(3), 423, 1974.
K. Saito, I. Hori, M. Higarashi, H. Midorikawa, Bull. Chem. Soc. Japan, 47(2), 476, 1974.

The oxidation base(s) in accordance with the invention preferably represent(s) from 0.0005 to 12% by weight approximately relative to the total weight of the ready-to-use dye composition, and even more preferably from 0.005 to 6% by weight approximately relative to this weight.

The couplers which can be used are those used conventionally in oxidation dye compositions, i.e. meta-phenylenediamines, meta-aminophenols and meta-diphenols, mono- or polyhydroxylated naphthalene derivatives, sesamol and its derivatives and heterocyclic compounds such as, for example, indole derivatives, indoline derivatives, benzimidazole derivatives, benzomorpholine derivatives, sesamol derivatives, pyrazoloazole derivatives, pyrroloazole derivatives, imidazoloazole derivatives, pyrazolopyrimidine derivatives, pyrazoline-3,5-dione derivatives, pyrrolo[3,2-d]oxazole derivatives, pyrazolo[3,4-d]thiazole derivatives, thiazoloazole S-oxide derivatives and thiazoloazole S,S-dioxide derivatives, and the addition salts thereof with an acid.

These couplers can be chosen in particular from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy) benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one and 1-phenyl-3-methylpyrazol-5-one, and the addition salts thereof with an acid.

When they are present, these couplers preferably represent from 0.0001 to 10% by weight approximately relative to the total weight of the ready-to-use dye composition, and even more preferably from 0.005 to 5% by weight approximately relative to this weight.

In general, the addition salts with an acid which can be used in the context of the dye compositions of the invention (oxidation bases and couplers) are chosen in particular from the hydrochlorides, hydrobromides, sulphates, tartrates, lactates and acetates.

The dye composition of the invention can also contain, in addition to the oxidation bases defined above and the optional combined couplers, direct dyes to enrich the shades with glints. These direct dyes can be chosen in particular from nitro dyes, azo dyes or anthraquinone dyes.

The subject of the invention is also a process for dyeing keratin fibres, and in particular human keratin fibres such as the hair, using the ready-to-use dye composition as defined above.

According to this process, at least one ready-to-use dye composition as defined above is placed on the fibres, for a period which is sufficient to develop the desired coloration, after which the fibres are rinsed, optionally washed with shampoo, rinsed again and dried.

The time required to develop the coloration on the keratin fibres is generally between 3 and 60 minutes and even more precisely between 5 and 40 minutes.

According to a first specific embodiment of the invention, the process includes a first step which consists in separately storing, on the one hand, a composition (A) comprising, in a medium which is suitable for dyeing, at least one oxidation base and optionally at least one coupler as defined above, and, on the other hand, a composition (B) containing, in a medium which is suitable for dyeing, at least one enzyme of 2-electron oxidoreductase type in the presence of at least one donor for the said enzyme and at least one nonionic guar gum containing at least one hydrophilic unit and at least one fatty chain, and then in mixing them together at the time of use, before applying this mixture to the keratin fibres.

According to another specific embodiment of the invention, the nonionic guar gum is incorporated into composition (A).

Another subject of the invention is a multi-compartment dyeing device or "kit" or any other multi-compartment packaging system, a first compartment of which contains composition (A) as defined above and a second compartment of which contains composition (B) as defined above. These devices can be equipped with means for applying the desired mixture to the hair, such as the devices described in patent FR-2,586,913 in the name of the Applicant.

A subject of the present invention is also a novel process for treating keratin substances, in particular the hair, in order to obtain a permanent reshaping of this hair, in particular in the form of permanent-waved hair, this process comprising the following steps: (i) a reducing composition is applied to the keratin substance to be treated, the keratin substance being placed under mechanical tension before, during or after the said application, (ii) the keratin substance is optionally rinsed, (iii) an oxidizing composition as defined above is applied to the optionally rinsed keratin substance, (iv) the keratin substance is optionally rinsed again.

The first step (i) of this process consists in applying a reducing composition to the hair. This application is carried out lock by lock or all at once.

The reducing composition comprises, for example, at least one reducing agent, which can be chosen in particular from thioglycolic acid, cysteine, cysteamine, glyceryl thioglycolate, thiolactic acid or thiolactic or thioglycolic acid salts.

The usual step for placing the hair under tension in a shape corresponding to the desired final shape for this hair (for example curls) can be carried out by any suitable means, in particular mechanical means, known per se for maintaining the hair under tension, such as, for example, rollers, curlers and the like.

The hair can also be shaped without the aid of external means, simply with the fingers.

Before carrying out the following optional rinsing step (ii), the hair onto which the reducing composition has been applied should, conventionally, be left to stand for a few minutes, generally between 5 minutes and one hour, preferably between 10 and 30 minutes, so as to give the reducing agent enough time to act correctly on the hair. This waiting phase preferably takes place at a temperature ranging from 35° C. to 45° C., while preferably also protecting the hair with a hood.

In the optional second step of the process (step (ii)), the hair impregnated with the reducing composition is then rinsed thoroughly with an aqueous composition.

Next, in a third step (step (iii)), the oxidizing composition of the invention is applied to the hair thus rinsed, with the aim of fixing the new shape given to the hair.

As in the case of the application of the reducing composition, the hair onto which the oxidizing composition has been applied is then, conventionally, left for a standing or waiting phase lasting a few minutes, generally between 3 and 30 minutes, preferably between 5 and 15 minutes.

If the hair was maintained under tension by external means, these means (rollers, curlers or the like) can be removed from the hair before or after the fixing step.

Lastly, in the final step of the process according to the invention (step (iv)), which is also optional, the hair impregnated with the oxidizing composition is rinsed thoroughly, generally with water.

Hair which is soft and easy to disentangle is finally obtained. The hair is wavy.

The oxidizing composition according to the invention can also be used in a process for bleaching keratin fibres, and in particular the hair.

The bleaching process according to the invention comprises a step of applying an oxidizing composition according to the invention to the keratin fibres in the presence or absence of an auxiliary oxidizing agent. Conventionally, a second step of the bleaching process according to the invention is a step of rinsing the keratin fibres.

The medium which is suitable for the keratin fibres (or the support) for the ready-to-use dye compositions and for the oxidation compositions used for the permanent reshaping or bleaching of keratin fibres in accordance with the invention generally consists of water or of a mixture of water and at least one organic solvent in order to dissolve the compounds which would not be sufficiently soluble in water. By way of organic solvent, mention may be made, for example, of $C_1$–$C_4$ alkanols such as ethanol and isopropanol; glycerol; glycols and glycol ethers such as 2-butoxyethanol, propylene glycol, propylene glycol monomethyl ether, diethylene glycol monoethyl ether and monomethyl ether, and aromatic alcohols such as benzyl alcohol or phenoxyethanol, similar products and mixtures thereof.

The solvents can be present in proportions preferably of between 1 and 40% by weight approximately relative to the total weight of the dye composition, and even more preferably between 5 and 30% by weight approximately.

The pH of the ready-to-use dye compositions and of the oxidizing compositions used for the permanent reshaping or bleaching of the keratin fibres in accordance with the invention is chosen such that the enzymatic activity of the 2-electron oxidoreductase is not adversely affected. It is generally between 5 and 11 approximately, and preferably between 6.5 and 10 approximately. It can be adjusted to the desired value using acidifying or basifying agents usually used for dyeing keratin fibres.

Among the acidifying agents, mention may be made, by way of example, of inorganic or organic acids such as hydrochloric acid, orthophosphoric acid, sulphuric acid, carboxylic acids such as acetic acid, tartaric acid, citric acid or lactic acid, and sulphonic acids.

Among the basifying agents, mention may be made, by way of example, of aqueous ammonia, alkaline carbonates, alkanolamines such as mono-, di- and triethanolamines, 2-methyl-2-aminopropanol and derivatives thereof, sodium hydroxide, potassium hydroxide and the compounds of formula (V) below:

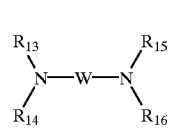

(V)

in which W is a propylene residue optionally substituted with a hydroxyl group or a $C_1$–$C_4$ alkyl radical; $R_{13}$, $R_{14}$, $R_{15}$ and $R_{16}$, which may be identical or different, represent a hydrogen atom or a $C_1$–$C_4$ alkyl or $C_1$–$C_4$ hydroxyalkyl radical.

The ready-to-use dye compositions and the oxidizing compositions for the permanent reshaping or bleaching of keratin fibres in accordance with the invention can also contain various adjuvants used conventionally in compositions for dyeing, permanently reshaping or bleaching the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, antioxidants, enzymes other than the 2-electron oxidoreductases used in accordance with the invention, such as, for example, peroxidases, penetration agents, sequestering agents, fragrances, buffers, dispersing agents, conditioners such as, for example, silicones, film-forming agents, preserving agents and opacifiers.

Needless to say, a person skilled in the art will take care to select this or these optional complementary compound(s) such that the advantageous properties intrinsically associated with the compositions in accordance with the invention are not, or are not substantially, adversely affected by the addition or additions envisaged.

The ready-to-use dye compositions and the oxidizing compositions used for the permanent reshaping or bleaching of keratin fibres in accordance with the invention can be in various forms, such as in the form of liquids, creams or gels, which are optionally pressurized, or in any other form which is suitable for dyeing, permanently reshaping or bleaching keratin fibres, and in particular human hair.

In the case of a ready-to-use dye composition, the oxidation dyes(s) and the 2-electron oxido-reductase(s) are present in the said composition, which must be free of oxygen gas, so as to avoid any premature oxidation of the oxidation dye(s).

Concrete examples illustrating the invention will now be given.

In the text hereinabove and hereinbelow, except where otherwise mentioned, the percentages are expressed on a weight basis.

The examples which follow illustrate the invention without being limiting in nature.

EXAMPLE 1

Dye Composition

The ready-to-use dye composition below was prepared (contents in grams):

Uricase from Arthrobacter globiformis at a concentration of 20 International Units (I.U.)/mg, sold by the company Sigma 1.5 g Uric acid 1.5 g ($C_8$–$C_{10}$)alkyl polyglucoside as an aqueous solution containing 60% active material (A.M.), sold under the name Oramix CG110 by the company SEPPIC 8.0 g Para-phenylenediamine 0.324 g Resorcinol 0.32 g Hydroxypropyl guar gum sold under the name Jaguar HP 60 by the company Mayhall 1.6 g Ethanol 20.0 g Monoethanolamine qs pH 9.5

Demineralized water qs 100 g

This ready-to-use dye composition was applied to locks of natural grey hair containing 90% white hairs for 30 minutes. The hair was then rinsed, washed with a standard shampoo and then dried.

Locks of hair dyed a matt dark-blond colour were obtained.

EXAMPLE 2

Oxidizing Composition for Permanent-waving or Bleaching

Uricase from *Arthrobacter globiformis* at a concentration of 20 International Units (I.U.)/mg, sold by the company Sigma 1.8 g Uric acid 1.65 g Ethanol 20.0 g ($C_8$–$C_{10}$)alkyl polyglucoside as an aqueous solution containing 60% active material (A.M.), sold under the name Oramix CG110 by the company SEPPIC 8.0 g Hydroxypropyl guar gum sold under the name Jaguar HP 60 by the company Mayhall 0.25 g 2-Methyl-2-amino-1-propanol qs pH 9.5

Demineralized water qs 100 g

What is claimed is:

1. A cosmetic or dermatological composition for treating keratin fibers comprising:
   at least one enzyme chosen from 2-electron oxidoreductases;
   at least one donor for said at least one enzyme; and
   at least one nonionic guar gum.

2. The composition of claim 1, wherein said 2-electron oxidoreductases are chosen from pyranose oxidases, glucose oxidases, glycerol oxidases, lactate oxidases, pyruvate oxidases and uricases.

3. The composition of claim 2, wherein said 2-electron oxidoreductases are chosen from uricases of animal, microbiological and biotechnological origin.

4. The composition of claim 1, wherein said at least one enzyme is present in an amount ranging from 0.01% to 20% by weight relative to the total weight of the composition.

5. The composition of claim 4, wherein said at least one enzyme is present in an amount ranging from 0.1% to 5% by weight relative to the total weight of the composition.

6. The composition of claim 1, wherein said at least one donor is chosen from D-glucose, L-sorbose, D-xylose, glycerol, dihydroxyacetone, lactic acid and its salts, pyruvic acid and its salts, and uric acid and its salts.

7. The composition of claim 6, wherein said at least one donor is chosen from uric acid and its salts.

8. The composition of claim 1, wherein said at least one donor is present in an amount ranging from 0.01% to 20% by weight relative to the total weight of the composition.

9. The composition of claim 8, wherein said at least one donor is present in an amount ranging from 0.1% to 5% by weight relative to the total weight of the composition.

10. The composition of claim 1, wherein said at least one nonionic guar gum is chosen from unmodified guar gums and chemically modified guar gums.

11. The composition of claim 10, wherein said chemically modified guar gums are modified with $C_1$–$C_6$ hydroxyalkyl groups.

12. The composition of claim 11, wherein said $C_1$–$C_6$ hydroxyalkyl groups are chosen from hydroxymethyl, hydroxyethyl, hydroxypropyl and hydroxybutyl groups.

13. The composition of claim 11, wherein said chemically modified guar gums modified with $C_1$–$C_6$ hydroxyalkyl groups have a degree of hydroxyalkylation ranging from 0.4 to 1.2.

14. The composition of claim 12, wherein said chemically modified guar gums modified with said $C_1$–$C_6$ hydroxyalkyl groups have a degree of hydroxyalkylation ranging from 0.4 to 1.2.

15. The composition of claim 1, wherein said at least one nonionic guar gum is present in an amount ranging from 0.01% to 10% by weight relative to the total weight of the composition.

16. The composition of claim 15, wherein said at least one nonionic guar gum is present in an amount ranging from 0.1% to 5% by weight relative to the total weight of the composition.

17. The composition of claim 1, further comprising at least one oxidation base.

18. The composition of claim 17, wherein said at least one oxidation base is chosen from para-phenylenediamines, double bases, ortho- and para-aminophenols, heterocyclic bases, and acid addition salts thereof.

19. The composition of claim 18, wherein said at least one oxidation base is chosen from:

para-phenylenediamine compounds chosen from: para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-2-methylaniline, 4-amino-2-chloro-N,N-bis(β-hydroxyethyl)aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, and acid-addition salts thereof;

double bases chosen from: N,N'-bis(β-hydroxyethyl)-N,N'-bis(4'-aminophenyl)-1,3-diaminopropanol, N,N'-bis(β-hydroxyethyl)-N,N'-bis(β'-aminophenyl) ethylenediamine, N,N'-bis(4-aminophenyl) tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylenediamine, 1,8-bis(2,5-diaminophenoxy)-3,5-dioxaoctane, and acid-addition salts thereof;

ortho-aminophenols chosen from: 2-aminophenol, 2-amino-5-methylphenol, 2-amino-6-methylphenol, 5-acetamido-2-aminophenol, and acid-addition salts thereof;

pyridine compounds chosen from: 2,5-diaminopyridine, 2-(4-methoxyphenyl)amino-3-amino-pyridine, 2,3-diamino-6-methoxypyridine, 2-(ÿ-methoxy-ethyl)amino-3-amino-6-methoxypyridine, 3,4-diaminopyridine, and acid-addition salts thereof;

pyrimidine compounds chosen from: 2,4,5,6-tetraamino-pyrimidine, 4-hydroxy-2,5,6-triaminopyrimidine, 2-hydroxy-4,5,6-triamino-pyrimidine, 2,4-dihydroxy-5,6-diaminopyrimidine, 2,5,6-tri-amino-pyrimidine, and acid-addition salts thereof;

pyrazole compounds chosen from: 4,5-diamino-1-methyl-pyrazole, 3,4-diaminopyrazole, 4,5-diamino-1-(4'-chlorobenzyl)pyrazole, 4,5-diamino-1,3-dimethyl-pyrazole, 4,5-diamino-3-methyl-1-phenylpyrazole, 4,5-diamino-1-methyl-3-phenylpyrazole, 4-amino-1,3-di-methyl-5-hydrazinopyrazole, 1-benzyl-4,5-diamino-3-methyl-pyrazole, 4,5-diamino-3-tert-butyl-1-methyl-pyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methyl-pyrazole, 4,5-diamino-3-hydroxymethyl-1-iso-propyl-pyrazole, 4,5-diamino-3-methyl-1-isopropyl-pyrazole, 4-amino-5-(2'-amino-ethyl)amino-1,3-dimethyl-pyrazole, 3,4,5-triamino-pyrazole, 1-methyl-3,4,5-tri-amino-pyrazole, 3,5-diamino-1-methyl4-methylamino-pyrazole, 3,5-diamino4-(β-hydroxyethyl)amino-1-methyl-pyrazole, and acid-addition salts thereof, and pyrazolopyrimidine compounds chosen from:
pyrazolo[1,5-a]pyrimidine-3,7-diamine,
2,5-dimethylpyrazolo[1,5-a]pyrimidine-3,7-diamine,
pyrazolo[1,5-a]pyrimidine-3,5-diamine,
2,7-dimethylpyrazolo[1,5-a]pyrimidine-3,5-diamine,
3-aminopyrazolo[1,5-a]pyrimidin-7-ol,
3-aminopyrazolo[1,5-a]pyrimidin-5-ol,
2-(3-aminopyrazolo[1,5-a]pyrimidin-7-ylamino) ethanol,
2-(7-aminopyrazolo[1,5-a]pyrimidin-3-ylamino) ethanol,
2-[(3-aminopyrazolo[1,5-a]pyrimidin-7-yl)-(2-hydroxy-ethyl)amino]ethanol,
2-[(7-aminopyrazolo[1,5-a]pyrimidin-3-yl)-(2-hydroxy-ethyl)amino]ethanol,
5,6-dimethylpyrazolo[1,5-a]pyrimidine-3,7-diamine,
2,6-dimethylpyrazolo[1,5-a]pyrimidine-3,7-diamine,
2,5,N7,N7-tetramethylpyrazolo[1,5-a]pyrimidine-3,7-diamine;

and addition salts thereof and the tautomeric forms thereof, when a tautomeric equilibrium exists.

20. The composition of claim 1, further comprising at least one coupler.

21. The composition of claim 20, wherein said at least one coupler is a meta-aminophenol coupler chosen from meta-aminophenol, 5-amino-2-methoxyphenol, 5-amino-2-(β-hydroxyethyloxy)phenol, 5-amino-2-methylphenol, 5-N-(β-hydroxyethyl)amino-2-methylphenol, 5-N-(β-hydroxyethyl)amino-4-methoxy-2-methylphenol, 5-amino-4-methoxy-2-methylphenol, 5-amino-4-chloro-2-methylphenol, 5-amino-2,4-dimethoxyphenol, 5-(γ-hydroxypropylamino)-2-methylphenol and acid-addition salts thereof.

22. The composition of claim 1, further comprising water or a mixture of water and at least one organic solvent.

23. The composition of claim 22, wherein said at least one organic solvent is present in an amount ranging from 1% to 40% by weight relative to the total weight of the composition.

24. The composition of claim 23, wherein said at least one organic solvent is present an amount ranging from 5% to 30% by weight relative to the total weight of the composition.

25. The composition of claim 1, said composition having a pH ranging from 5to 11.

26. The composition of claim 25, wherein said pH ranges from 6.5 to 10.

27. The composition of claim 1, further comprising at least one adjuvant chosen from anionic, cationic, nonionic, amphoteric and zwifterionic surfactants; anionic, cationic, nonionic, amphoteric and zwitterionic polymers; inorganic and organic thickeners, antioxidants, enzymes other than said at least one enzyme chosen from 2-electron oxidoreductases, penetration agents, sequestering agents, fragrances, buffers, dispersing agents, conditioners, film-forming agents, preserving agents and opacifiers.

28. The composition of claim 1, wherein said composition comprises:

- at least one 2-electron oxidoreductase enzyme chosen from pyranose oxidases, glucose oxidases, glycerol oxidases, lactate oxidases, pyruvate oxidases and uricases;
- at least one donor for said at least one enzyme chosen from D-glucose, L-sorbose, D-xylose, glycerol, dihydroxyacetone, pyruvic acid and its salts, lactic acid and its salts, and uric acid and its salts; and
- at least one nonionic guar gum chosen from unmodified guar gums and chemically modified guar gums, wherein said chemically modified guar gums are modified with $C_1$–$C_6$ hydroxyalkyl groups chosen from hydroxymethyl, hydroxyethyl, hydroxypropyl and hydroxybutyl groups, wherein said $C_1$–$C_6$ hydroxyalkyl groups have a degree of hydroxyalkylation ranging from 0.4 to 1.2.

* * * * *

UNITED STATES PATENT AND TRADEMARK OFFICE
CERTIFICATE OF CORRECTION

PATENT NO.   : 6,241,784 B1
DATED        : June 5, 2001
INVENTOR(S)  : De La Mettrie et al.

It is certified that error appears in the above-identified patent and that said Letters Patent is hereby corrected as shown below:

Column 15, claim 19,
Line 37, "bis ($\beta$'-" should read -- bis(4'- --.

Column 16, claim 19,
Line 11, "diamino4" should read -- diamino-4 --.

Signed and Sealed this

Fifth Day of March, 2002

Attest:

JAMES E. ROGAN
*Attesting Officer*   *Director of the United States Patent and Trademark Office*